United States Patent [19]

Knifton

[11] Patent Number: 5,349,110
[45] Date of Patent: Sep. 20, 1994

[54] SYNTHESIS OF LOW MOLECULAR WEIGHT GLYCOL ETHERS FROM OXIRANES PLUS OLEFINS

[75] Inventor: John F. Knifton, Austin, Tex.

[73] Assignee: Texaco Chemical Company, White Plains, N.Y.

[21] Appl. No.: 100,792

[22] Filed: Aug. 2, 1993

Related U.S. Application Data

[62] Division of Ser. No. 569,308, Aug. 20, 1990, abandoned.

[51] Int. Cl.$^5$ .............................................. C07C 41/02
[52] U.S. Cl. ................................... 568/678; 568/695; 568/867; 568/897
[58] Field of Search ................ 568/678, 897, 695, 867

[56] References Cited

U.S. PATENT DOCUMENTS

| | | | |
|---|---|---|---|
| 3,996,298 | 12/1976 | Izumi et al. | 568/901 |
| 4,236,034 | 11/1980 | Aoshima et al. | 568/901 |
| 4,277,632 | 7/1981 | Kumazawa et al. | 568/867 |
| 4,376,219 | 3/1983 | Murofushi et al. | 568/678 |

FOREIGN PATENT DOCUMENTS 14909  2/1979  Japan .................. 568/697

2050372  1/1981  United Kingdom .......... 568/678

*Primary Examiner*—Howard T. Mars
*Attorney, Agent, or Firm*—Russell R. Stolle; Cynthia L. Kendrick

[57] ABSTRACT

Disclosed is a process for preparation of monoalkyl ethers by reacting low molecular weight olefins and the corresponding oxiranes, in the presence of a catalyst comprising an acidic heterogeneous or homogeneous catalyst, generally represented by the equation:

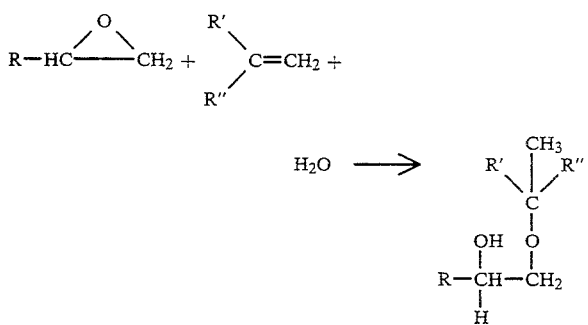

where R, R', R" may be hydrogen or an alkyl radical.

1 Claim, No Drawings

SYNTHESIS OF LOW MOLECULAR WEIGHT GLYCOL ETHERS FROM OXIRANES PLUS OLEFINS

This is a continuation, division, of application Ser. No. 07/569,308, filed Aug. 20, 1990 and now abandoned.

This invention relates to the synthesis of glycol monoalkyl ethers, and more particularly this invention relates to a process for the synthesis of ethylene and propylene glycol monoalkyl ethers from low molecular weight olefins and the corresponding oxirane using acidic homogeneous or heterogeneous catalysts. The acidic catalysts include heteropoly acids, acidic montmorillonite clays, including Lewis acid and Bronsted acid modified clays, sulfonic acid resins and perfluorinated sulfonic acid resins. This is a new route to these products and the invention is particularly advantageous in that the desired monoalkyl ethers have been prepared in good selectivity with substantial oxirane conversion levels. In addition, the process requires only moderate temperatures. There is an expanding market for higher molecular weight propylene and ethylene glycol monoalkyl ethers because they can be substituted for ethylene glycol monomethyl ether and ethylene glycol monoethyl ether in solvent formulations, since the latter have been determined to be carcinogenic.

BACKGROUND OF THE INVENTION

Low molecular weight glycol ethers and their acetate derivatives are widely used as solvents in paints and coatings. In 1984, the EPA issued guidelines to reduce exposure to 2-methoxyethanol, 2-ethoxyethanol and their acetates since studies indicated these chemicals were carcinogens.

Ethylene glycol monobutyl ether plays an important role in waterborne coatings, accounting for about 80% of glycol ether content, but has not been implicated in any studies as a tetrogen. Many solvents have been reformulated in recent years to use heavier propylene glycol and ethylene glycol monobutyl ethers rather than lighter ethylene glycol monomethyl and ethyl ethers (see for example European Patent Application 288-856A).

Methods of preparing ethylene and propylene glycol mono-n-butyl ethers are known in the art. For example, one method for preparation is by the reaction of ethylene oxide or propylene oxide and n-butanol.

Another method of synthesizing low molecular weight ethers is disclosed in U. S. Pat. No. 4,714,787 which discloses a process for selectively reacting one or more linear monoolefins with a primary or secondary lower molecular weight alcohol to form the corresponding ethers. The active acidic catalyst component is a sulfonate ion-exchange resin or a crystalline silicate having a pore size greater than 5 A.U. In the preferred embodiment, methanol and propylene are reacted to selectively form methyl isopropyl ether and the preferred crystalline silicate includes a crystalline zeolite having a silica to alumina mole ratio greater than about 12. Here the main products are methyl isopropyl ether and dimethyl ether.

In U. S. Pat. No. 4,675,082 there is disclosed a method for preparation of 1-t-butoxy-2-propanol from the etherification of propylene glycol with isobutylene in the presence of a solid resin etherification catalyst, typically an acidic ion exchange resin such as AMBERLYST®-15, consisting of sulfonated polystyrene matrix having up to about 25% of copolymerized divinylbenzene bearing functional sulfonic acid groups contained therein. This process requires a two tower separation.

Polyethylene glycol and propylene are reacted to form polyethylene glycol dipropyl ethers using a strongly acidic cation resin as a catalyst. This process provides good yields of polyethylene glycol dipropyl ethers by reducing side reactions such as polymerization and decomposition. See reference (J58052321-A or J8 8037819-B) in Derwent Japanese Patents Abstract, Polymer+General Chemistry, Vol. 88, No. 30. In a Japanese reference to the same company, Nippon Shokubai Kagaku, polyethylene glycol is reacted with isobutylene to produce polyethylene glycol dibutyl ether (J58049725-A).

The preparation of propylene glycol tert-butyl ether from propylene glycol and isobutylene is disclosed in Jpn. Kokai Tokkyo Koho JP 63,250,336 to Fujiwara, Hiroshi et al. (Maruzen). A strongly acidic cation-exchanger resin is employed along with tert-butanol ($Me_3COH$) which serves to inhibit the formation of by-product diisobutylene. The reaction product must be distilled to separate propylene glycol tert-butyl ether from propylene glycol di-tert butyl ether.

Methods of using clays as catalysts for certain reactions are known in the art. In Chem. Systems, Topical Reports, Vol. II, 1986 Program (May 1987), Section 3.00, there is an article which introduces the subject of pillared clays. There it is disclosed that several processes can employ these pillared clay catalysts and that propylene glycol ethers are of particular interest, since, as mentioned, corresponding ethylene glycol ethers are believed to be toxic. Further, it is stated that alkylene glycol ethers are conventionally prepared by the interaction of an alcohol with an epoxide. Generally a catalyst such as sodium hydroxide or an alkali metal alcoholate is used, together with a tenfold excess of alcohol.

There is art available which has focused on how various factors affect clay catalysts. In an article titled "Pillared Clays As Catalysts" in *Catal. Rev.-Sci. Eng.*, 30(3), 457–499 (1988) there is a discussion of factors affecting the thermal stability of pillared clays and how the stability can be improved in the range from about 480° C. to about 800° C. The same article also discusses the acidity of pillared clays and ways in which different treatments affect the Lewis or Bronsted sites to a varying extent.

Stabilized pillared interlayered clays are used in the invention of EP 0083 970 to carry out processes capable of catalysis by protons. The invention included methods for preparing alcohols from olefins or olefin oxides and water, or ethers from primary or secondary aliphatic alcohols, a polyol or an olefin oxide.

An interesting comparison of montmorillonite-derived catalysts with ion-exchange resins as it relates to one particular reaction is found in an article titled "Methyl-t-Butyl Ether (MTBE) Production: A Comparison Of Montmorillonite Derived Catalysts With An Ion-Exchange Resin", Adams, et al. *Clays and Clay Minerals*, Vol. 34., No. 5, 597–603, 1986. Here it is concluded that $Al^{+3}$-clay has greater catalytic activity than acid treated-clay (K10) which has greater activity than ACH-treated clay which is approximately the same as pillared clay. Further, the activity of $Al^{+3}$ montmorillonite at 60° C. is about 50% of that exhibited by an acidic ion-exchange resin similar to that used industrially.

Research performed by Adams, et al., at the University of Wales involved the acid-catalyzed reaction between methanol and isobutene to give methyl-t-butyl ether. These researchers found that where cation-exchanged smectite was used as the catalyst, the clays which had been exchanged with monovalent divalent cations gave low yields in comparison with clays exchanged with trivalent ions. See "Synthesis Of Methyl-t-Butyl Ether From Methanol And Isobutene Using A Clay Catalyst", Adams, et al., *Clay and Clay Minerals*, Vol. 30, No. 2, 129-134, 1982.

It is always advantageous to prepare chemicals for which there is a demand from inexpensive feedstocks or feedstocks that are readily available, or a by-product of some chemical process. It would be a distinct advance in the art if a process were available which allowed for the continuous production of low molecular weight glycol monoalkyl ethers, particularly glycol mono-t-butyl and mono-isopropyl ethers in high selectivity and conversion from readily available, and inexpensive, oxirane/olefin feedstock combinations. Furthermore, it would be advantageous if this reaction was one-step, did not require any second distillation and the catalyst was physically and chemically stable to the reactant/product media over a broad range of temperatures, particularly above 100° C., so that there were minimal problems with catalyst decomposition and loss activity.

It has been surprisingly discovered that several different classes of acidic catalysts can be used to synthesize ethylene and propylene glycol ethers from the corresponding olefins and oxiranes. It is particularly an object of the present invention to recover mono-t-butyl ethers in a high state of purity with minimal amounts of by-products. Other objects will become apparent to those skilled in the art from the following description.

SUMMARY OF THE INVENTION

In accordance with the foregoing, the novel method of this invention for synthesis of glycol monoalkyl ethers comprises reacting low molecular weight olefins and the corresponding oxirane in the presence of a strong acid catalyst, either homogeneous or heterogeneous.

The desired glycol monoalkyl ethers have been prepared with selectivity as high as 25%, at high olefin conversion levels. Both batch and continuous synthesis can be used.

DESCRIPTION OF THE INVENTION

Preparation of the glycol monoalkyl ether products of this invention may be carried out preferably by reacting an oxirane with a low molecular weight olefin batchwise, or continuously, in the presence sufficient water to satisfy the stoichiometry of Eq. 1 below and in the presence of a catalyst comprising an acidic homogeneous or heterogeneous catalyst. The products include propylene glycol mono-t-butyl ether, propylene glycol mono-isopropyl ether, ethylene glycol mono-isopropyl ether, and ethylene glycol mono-t-butyl ether.

The general synthesis is illustrated by the following equation:

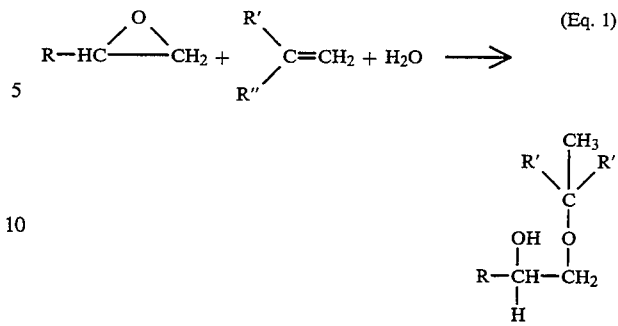

where R, R', R" may be hydrogen or an alkyl radical.

Both linear and isoalkenes, as well as mixtures thereof, are useful in the process of this invention, including olefins of carbon number 2 to 20. Branched chain terminal olefins are preferred. Useful terminal olefins include isobutylene and mixed terminal olefins of the $C_{10}$–$C_{14}$ and $C_{11}$–$C_{13}$ carbon range. The structure can be represented by:

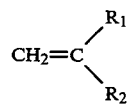

wherein $R_1$ and $R_2$ individually are hydrogen or alkyl groups and the total carbon atoms in $R_1+R_2$ is from 0 to 18. The preferred linear or isoalkenes are alpha olefins having 3 to 5 carbon atoms, i.e. the total carbon atoms in $R_1+R_2$ is 1 to 3. These olefins include propylene, 1-butene, isobutylene, 1-pentene, 2-pentene, 2-methyl-1-butene and isoamylene. Particularly preferred alpha olefins are propylene and isobutylene- Said olefins may be employed in diluted form, e.g. the isobutylene may be contained in a typical $C_4$ stream (from an ethylene plant).

Suitable oxiranes include ethylene oxide, propylene oxide, isobutylene oxide, 1-butylene oxide as well as other aliphatic epoxides containing from 2 to 20 carbon atoms. The preferred oxiranes for the generation of glycol monoalkyl ethers using acidic catalysts are oxides containing 2 to 6 carbon atoms per molecule. These include ethylene oxide and propylene oxide.

The molar ratio of said oxiranes and olefins in the feed mixture may vary widely, from at least 100:1 to 1:100. To achieve optimum selectivities and yields of desired glycol monoalkyl ethers (Eq. 1), it is desirable that the feed should be rich in the oxirane component, i.e. the molar feed ratio of oxirane-to-olefin should be greater than unity. On the other hand, if it is desirable to make glycol dialkyl ethers, then the feed should be rich in olefin and the same molar ratio should be less than unity. These conditions are consistent with the accompanying examples.

As stated the invention involves five classes of acidic homogeneous and heterogeneous catalysts, including:
a) Acidic montmorillonite clays, such as Engelhard Clay-24.
b) Heteropoly acids such as 12-tungstophosphoric acid.
c) Sulfonic acid resins such as AMBERLYST® XN-1010 and AMBERLITE®IR-118.
d) Perfluorinated membranes and beads of NAFION®.

e) Modified acidic clays where the modifying agent is either a Lewis acid, such as zirconium(IV) chloride, or a Bronsted acid, like 12-tungstophosphoric acid.

In the first embodiment the clays used as the basis of the catalyst to effect this reaction are acidic montmorillonite silica-alumina clays. A variety of clay catalysts containing aluminum and silica can be effective in the subject reaction (Eq. 1), however it is necessary that the alumina or silica be acidic under normal operating conditions. As discussed, a group of catalysts which work well in this synthesis are acidic clay mineral catalysts. Chemically clays are composed primarily of silicon, aluminum and oxygen, with minor amounts of magnesium and iron in some cases. Variations in the ratios of these constituents, and their crystal lattice configurations, result in some fifty separate clays, each with its own characteristic properties.

One group of acidic clays are smectite clays. These clays have small particle size and unusual intercalation properties which afford them high surface area. They are alumino silicates having a unique structure that permits modifications which provide useful catalysts. They comprise layered sheets of octahedral sites between sheets of tetrahedral sites, and the distance between the layers can be adjusted by swelling, through treatment with the appropriate solvent, or treatment with a pillaring or Lewis acid reagent etc. What renders the smectites of particular interest among the clay minerals is their combination of cation exchange, intercalation and swelling properties.

The three-layer sheet types of smectite clays include montmorillonite, vermiculite and certain micas, all of which may be expanded between their layers by the appropriate treatment. The idealized basic structure of clays of this type is that of a pyrophyllite which has the basic formula $Si_8Al_4O_{20}(OH)_4$.

A general representation of the montmorillonite structure which is particularly useful is:

$$M_{x/n}^{n+} \cdot yH_2O(Al_{4-x}Mg_x)(Si_8)O_{20}(OH)_4$$

where M represents the interlamellar (balancing) cation, normally sodium or lithium and x, y and n are integers.

Acidic montmorillonite clays are the preferred form of smectite clay in the present invention. Acids, particularly mineral acids such as sulfuric acid, activate montmorillonites by attacking and solubilizing structural cations in the octahedral layers. This opens up the clay structure and increases surface area. Preferably these acid clays should have acidities in the range of 3 to 20, or greater, mg KOH/gm, titrated to a phenolphthalein end point. Their surface area should be >30 m²/g, and preferably 200 to 1000 m²/g. Their moisture content should also be limited, which can be accomplished by heating to about 220° F., by which method the weight loss is generally less than 20 wt %.

Illustrative examples of suitable montmorillonite clays include powdered clays such as Filtrol Grade 13, 113 and 160, sold by Engelhard, clays in granular form, such as Filtrol Grade 24, having a 20-60 mesh size, and grade 25 (10/20 mesh) sold by Engelhard, as well as extruded clays such as the Filtrol Clay-62, sold in 1/16" and 3/16" diameter extrudates.

In the second embodiment, the heteropoly acids that are catalysts in the subject reaction comprise a class of acids formed by the condensation of two or more inorganic oxyacids. For example, phosphate and tungstate ions, when reacted in an acidic medium, are condensed to form 12-tungstophosphoric acid, a typical heteropoly acid (HPA) according to Equation 2:

$$PO_4^{3-} + 12WO_4^{2-} + 27H^+ \rightarrow H_3PW_{12}O_{40} + 12H_2O \quad \text{(Eq. 2)}$$

A wide variety of elements ranging from Group I to Group VIII can become the central atom of the HPA anion, or the: heteroatom as it is called (P in the case of Eq. 2). The nature of the heteroatom is a governing factor which determines both the condensation structure and the physical properties of the HPA.

Atoms coordinated to the heteroatom via oxygens are called polyatoms (W in the case of Eq. 2) and in most cases are any one of such limited species as molybdenum, tungsten, niobium and vanadium. In the case of molybdenum (Mo) as the polyatom, the nature of the heteroatoms, condensation ratios and chemical formulae of the corresponding HPA anions are summarized in Table I.

Anions containing the so-called Keggin structure have a condensation ratio of 1:12 and are the most typical of all HPA anions. Heteropoly acids with the Keggin structure, and their homologues, are generally the most readily available HPA's and the ones most commonly used in catalysis. The synthesis of these HPA's is well documented in the literature (see for example U.S. Pat. No. 3,947,332 (1976).

TABLE I

| | Typical heteropolymolybdate anions | | |
|---|---|---|---|
| CONDENSATION RATIOS | | HETERO ATOMS (X) | CHEMICAL FORMULAS |
| 1:12 | Keggin structure | $P^{5+}, As^{5+}, Si^{4+}, Ge^{4+}$ | $[X^{n+}Mo_{12}O_{40}]^{-(8-n)}$ |
| | Silverton structure | $Ce^{4+}, Th^{4+}$ | $[X^{4+}Mo_{12}O_{42}]^{8-}$ |
| 1:11 | Keggin structure (decomposition) | $P^{5+}, As^{5+}, Ge^{4+}, Si^{4+}$ | $[X^{n+}Mo_{11}O_{39}]^{-(12-n)}$ |
| 2:18 | Dawson structure | $P^{5+}, As^{5+}$ | $[X_5^{5+}Mo_{18}O_{62}]^{6-}$ |
| 1:9 | Waugh structure | $Mn^{4+}, Ni^{4+}$ | $[X^{4+}Mo_9O_{32}]^{6-}$ |
| 1:6 | Anderson structure (A type) | $Te^{6+}, I^{7+}$ | $[X^{n+}Mo_6O_{24}]^{-(12-n)}$ |
| | (B type) | $Co^{3+}, Al^{3+}, Cr^{3+}$ | $[X^{n+}Mo_6O_{24}H_6]^{-(6-n)}$ |
| 4:12 | | $As^{5+}$ | $[H_4As_4Mo_{12}O_{52}]^{4-}$ |
| 2:5 | | $P^{5+}$ | $[P_2Mo_5O_{23}]^{6-}$ |

In the case of synthesis of glycol ethers, suitable heteropoly acid catalysts may contain polyatoms selected from the group molybdenum, tungsten, niobium and vanadium, while the heteroatoms may be phosphorus, silicon, germanium, and arsenic. Preferably the heteroatoms are phosphorus or silicon. These heteropoly acids would likely have the Keggin structure, $H_{8-n}[XM_{12}O_{40}]$, were X = P or Si, M = Mo or W and n is an integer, 4 or 5.

The preferred heteropoly acids for the practice of this invention include 12-molybdophosphoric acid, $H_3PMo_{12}O_{40}$, 12-tungstophosphoric acid, molybdosilicic acid, $H_4SiMo_{12}O_{40}$ and tungstosilicic acid. Said acids are generally used as their hydrates; they may be employed by themselves, partially or completely dissolved in the olefin/oxirane feed, or they may be employed as heterogeneous catalysts bonded to a suitable support.

In the third embodiment the acid catalysts are a class of ion exchange resins with strongly acidic cation exchange. These include the gel type or macroreticular ion exchange groups, wherein the sulfonic acid function is bonded directly or indirectly to an organic polymer backbone, particularly an organic polystyrene, or styrene-divinylbenzene polymer having about 1 to 20% cross-linking. Examples of such resins include the AMBERLYST®15 and XN-1010, AMBERLITE®IR-118, DOWEX®50 ×2-100 and 5 ×8-100, XL-383 and -386, plus BIO RAD®A650 W-X2 and AMBERSEP®252H.

In the fourth embodiment the suitable heterogeneous catalyst system generally comprises a perfluorinated, ion-exchange resin. The perfluorinated ion-exchange catalysts useful in this invention are solid, superacidic, perfluorinated resin-sulfonic acid catalyst systems. Examples include NAFION®501 and NAFION®511 granules, NAFION®520 and 530 pellets, and NAFION®810 and NAFION®811 tubing, as well as other high acidity NAFION® membranes prepared, for example, from NAFION®117 perfluorinated membrane, and in the hydrogen ion form. NAFION® is the registered trademark for a cation exchange membrane developed by DuPont which is based on a poly(tetrafluorethylene) backbone with sulfonic acid groups attached at the end of the short side chains based on the perfluoropropylene ether unit, represented by the following structure:

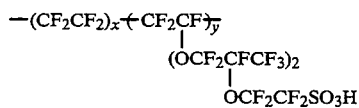

The catalysts of the last embodiment include acid activated clay catalysts. The performance of said acid modified montmorillonite clays in the subject synthesis of monoalkylethers from low molecular weight olefins plus oxiranes (Eq. 1) may be further enhanced by additional modification of the structure of said acidic clays, for example, by modification with certain Bronsted acids or Lewis acids. In particular it has been unexpectedly discovered that modification of the montmorillonite clays with heteropoly acids improves the performance of said clays by bringing about improvements both in terms of productivity and monoalkylether selectivity.

The heteropoly acids that are useful in the subject reaction comprise a class of acids formed by the condensation of two or more inorganic oxyacids as discussed above.

In the case of preparation of monoalkylethers, suitable heteropoly acid catalysts may contain polyatoms selected from the group molybdenum, tungsten, niobium and vanadium, while the heteroatoms may be phosphorus, silicon, germanium, and arsenic. Preferably the heteroatoms are phosphorus or silicon. These heteropoly acids would likely have the Keggin structure, $H_{8-n}[XM_{12}O_{40}]$, where $X=P$ or $Si$, $M=Mo$ or $W$ and $n$ is an integer which is 4 or 5.

The preferred heteropoly acids for the practice of this invention include 12-molybdophosphoric acid, molybdosilicic acid, 12-tungstosilicic acid and, especially, 12-tungstophosphoric. Said acids are generally used as their hydrates. Said montmorillonite clays may be treated with heteropoly acids by any number of techniques, but generally it is most convenient to treat the clay with a solution of heteropoly acid in water, or suitable organic solvent, using the incipient wetness technique. The modified clays are then dried and calcined.

The weight percent of heteropoly acid to montmorillonite clay should be such that the concentration of the polyatom (Mo, W, Nb or V) in the formulated catalyst is in the range of 0.1 wt % to 30 wt %, although concentrations outside this range may also be employed. In the preparation of 12-tungstophosphoric acid-on-clay catalyst, the tungsten content may be 0.1 to 20 wt %.

Said heteropoly acid modified montmorillonite clay catalysts perform as well, or better in the desired reaction (Eq. 1) than standard literature catalysts, such as the acidic ion-exchange resins. This improved performance is illustrated in the accompanying examples.

The performance of modified montmorillonite clays in the synthesis of monoalkylethers may also be further enhanced by modification of the structure of said acidic clays by treatment with certain Group IIIA and Group IVA derivatives.

The Group IVA derivatives that are useful in the subject reaction include Group IVA salts, oxides and complexes, but particularly their halide salts. Preferred reactants include titanium(IV) chloride, zirconium(IV) chloride and titanium(IV) bromide. The preferred Group IVA derivatives are their salts, particularly zirconium(IV) chloride.

The clays may be treated with these Group III or IVA derivatives by any number of techniques, but generally it is most convenient to treat the clay either by vapor deposition or with a solution or suspension of such Group III or IVA derivative in water, or a suitable organic solvent, using the incipient wetness technique. The modified clays are then dried and calcined.

The weight percent of Group III or IVA derivative to montmorillonite clay should be such that the concentration of the aluminum, titanium or zirconium in the formulated catalyst is in the range of 0.1 to 20 wt %, although concentrations outside this range may also be employed.

A solvent may optionally be added to facilitate the desired glycol ether synthesis. Suitable solvents include polar organic solvents containing one or more ether linkages or non-polar polyether solvents. Examples of satisfactory solvents include p-dioxane, 1,3-dioxane, 1,3-dioxolane, triglyme and tetraglyme. Glycol monoalkyl ethers may also serve as suitable solvents for the reaction in Eq. 1; this includes the product glycol monoalkyl ethers such as ethylene glycol t-butyl ether and the propylene glycol mono-t-butyl ethers.

The low molecular weight ether synthesis may be conducted batchwise, in a continuous slurry bed reactor, or in a fixed-bed, continuous flow, reactor. For practical reasons a fixed bed process is preferred.

Synthesis of ethylene and propylene glycol ethers can generally be conducted at temperatures from 0° to 300° C.; the preferred range is 25° to 200° C. The operating pressure may be from zero to 1000 psig, or higher. The preferred pressure range is 100 to 400 psig. Optimum conditions may vary depending on the reactants and specific catalyst used.

The principal ether products produced depend upon the olefin and oxirane charged. In the case of ethylene oxide, the addition of isobutylene results in ethylene glycol mono-t-butyl ether as the principal product. Where propylene oxide is the feedstock the addition of isobutylene results in the production of propylene glycol mono-t-butyl ethers. The majority monoalkyl glycol ether products are formed in accordance with the Markovnikov rule of addition to the double bond of an olefin.

The resultant reaction mixture, containing desired glycol ether product, undesired by-products and unreacted reactants such as olefin, are normally separated in a conventional manner by fractional distillation.

The principal by-products of these syntheses include glycols (such as ethylene glycol and propylene glycol), polyols (including the dipropylene glycols and tripropylene glycols), polyolmonoalkyl ethers, such as the diethylene glycol monoalkyl ethers, alcohols (such as t-butanol) as well as dioxolane derivatives.

Typically, desired glycol monoalkyl ethers are generated at liquid hourly space velocities (LHSV) of 1 to 5 under mild conditions. LHSVs of 5, or greater, have also been demonstrated to be useful in achieving satisfactory olefin conversion levels.

Here LHSVs is defined as follows:

$$LHSV = \frac{\text{Volume Of Total Liquid Feed Run Through The Reactor Per Hour}}{\text{Volume of Catalyst in Reactor}}$$

Conversion of olefin (wt %) in the following Examples is estimated in the following examples using the equation:

$$\frac{\text{Weight of [Olefin in Feed} - \text{Olefin in product]}}{\text{Weight of Olefin in Feed}} \times 100$$

Selectivities to glycol monoalkyl ether (mole%) are estimated from:

$$\frac{\text{Moles of Glycol Monoalkyl Ether Produced}}{\text{Moles of Olefin Converted}} \times 100$$

The accompanying examples illustrate the following facets of this invention:

1) The synthesis of propylene glycol mono-t-butyl ethers from propylene oxide plus isobutylene using an acidic montmorillonite clay catalyst (Engelhard Clay-24 granules) over a range of operating temperatures (80°–180° C., see Examples 1–4).
2) The same synthesis of propylene glycol mono-t-butyl ethers has been demonostrated using various heteropoly acid catalysts, including 12-tungstophosphoric acid and 12-molybdophosphoric acid, over a range of temperatures (see Examples 5–7 and 13). Here it is noteworthy that in Example 5, the estimated selectivity to propylene glycol mono-t-butyl ethers (basis isobutylene converted) is about 25 mole%.
3) A variety of other solid acid catalysts are effected for the desired glycol monoalkyl ether synthesis including:
    a) Sulfonic acid resins such as AMBERLYST ®XN-1010 and AMBERLITE ®IR-118.
    b) Perfluorinated resins such as NAFION ®NR50 beads.
    c) Modified acidic clays, including Engelhard Grade-24 granules modified with either zirconium tetrachloride or 12-tungstophosphoric acid.

These data are summarized in Examples 8–12, see Table II.

4) Ethylene glycol mono-t-butyl ether may likewise be prepared by similar procedures starting from ethylene oxide plus isobutylene using either acidic montmorillonite clays (Example 14) or heteropoly acid catalysts, such as 12-tungstophosphoric acid (Example 15).
5) Finally, the synthesis of propylene glycol mono-isopropyl ether from propylene oxide plus propylene has been demonstrated (see Example (see Example 16).

EXAMPLE 1

Synthesis of Propylene Glycol Mono-t-Butyl Ethers

To a 300 cc pressure reactor fitted with heating, mixing and temperature control was charged a mixture of propylene oxide (58.0 g, 1.0 mole), distilled water (20.0g) and acidic montmorillonite clay (Engelhard Clay-24 granules acidity 16 mg KOH/g, 5.0 g). The reactor was flushed with nitrogen and pressured with isobutylene (28.0 g, 0.5 mole), then heated to 180° C. with mixing. After 4 hours at temperature, the reactor was cooled and the product (95.4 g) recovered.

After removal of the clay granules by filtration, the pale yellow liquid product was analyzed by gc and gc-ir. Analysis showed the presence of:

| Propylene Glycol Mono-t-Butyl Ethers: | |
| --- | --- |
| 1-(t-butoxy)-2-propanol | 6.4% |
| 2-(t-butoxy)-1-propanol | 0.9% |
| Propylene glycol di-t-butyl ether | 0.4% |
| Propylene glycol | 23.9% |
| t-Butanol | 12.7% |
| Isobutylene | 1.6% |

Also present were significant quantities of dipropylene glycol (3 isomers) and tripropylene glycols (6 isomers) as well as dioxolane derivatives.

EXAMPLE 2–4

Synthesis of Propylene Glycol Mono-t-Butyl Ethers

Following the procedures of Example 1, propylene oxide (58.0 g, 1.0 mole), distilled water (20.0g) and isobutylene (28.0 g, 0.5 mole) were charged to a 300 cc pressure reactor containing Engelhard Clay-24 granules (5.0g) and the mixtures heated to a prescribed temperature, from 80° to 120° C., with mixing. After 4 hours at temperature, the reactor was cooled and the product recovered, filtered and the liquid analyzed.

When the reaction was run at 120° C, the product (102g) comprised:

| Propylene Glycol Mono-t-Butyl Ethers: | |
| --- | --- |
| 1-(t-butoxy)-2-propanol | 8.8% |
| 2-(t-butoxy)-1-propanol | 1.1% |
| Propylene glycol di-t-butyl ether | 0.8% |
| Propylene glycol | 17.4% |
| t-Butanol | 21.7% |
| Isobutylene | 2.3% |

Where the reaction was run at 100° C., the product (87g) comprised:

| Propylene Glycol Mono-t-Butyl Ethers: | |
|---|---|
| 1-(t-butoxy)-2-propanol | 7.4% |
| 2-(t-butoxy)-1-propanol | 1.5% |
| Propylene glycol di-t-butyl ether | 0.4% |
| Propylene glycol | 21.7% |
| t-Butanol | 17.5% |
| Isobutylene | 1.8% |

Where the reaction was run at 80° C., the product (83g) comprised:

| Propylene Glycol Mono-t-Butyl Ethers: | |
|---|---|
| 1-(t-butoxy)-2-propanol | 0.5% |
| 2-(t-butoxy)-1-propanol | 0.3% |
| Propylene glycol | 34.1% |
| t-Butanol | 1.3% |
| Isobutylene | 0.6% |

EXAMPLE 5

To a 300 cc pressure reactor fitted with heating, mixing and temperature control was charged a mixture of propylene oxide (58.0 g, 1.0 mole), distilled water (20.0g) and 12-tungstophosphoric acid (5.0g). The reactor was flushed with nitrogen and pressured with isobutylene (28.0 g, 0.5 mole), then heated to 100° C. with mixing. After 4 hours at temperature, the reactor was cooled and the product (123g) recovered.

Analyses of the water-white liquid product showed the presence of:

Propylene Glycol Mono-t-Butyl Ethers:

When the reaction was run at 120° C., the product (123g) comprised:

| Propylene Glycol Mono-t-Butyl Ethers: | |
|---|---|
| 1-(t-butoxy)-2-propanol | 7.2% |
| 2-(t-butoxy)-1-propanol | 0.8% |
| Propylene glycol di-t-butyl ether | 0.7% |
| Propylene glycol | 14.3% |
| t-Butanol | 15.1% |
| Isobutylene | 7.4% |

Where the reactor was run at 80° C., the product (106g) comprised:

| Propylene Glycol Mono-t-Butyl Ethers: | |
|---|---|
| 1-(t-butoxy)-2-propanol | 7.9% |
| 2-(t-butoxy)-1-propanol | 1.1% |
| Propylene glycol di-t-butyl ether | 1.0% |
| Propylene glycol | 17.7% |
| t-Butanol | 21.5% |
| Isobutylene | 6.0% |

EXAMPLES 8-12

Syntheses of Propylene Glycol Mono-t-Mutyl Ethers

Following the procedures of Example 1, propylene oxide (58.0 g, 1.0 mole), distilled water (20.0g) and isobutylene (28.0 g, 0.5 mole) were charged to a 300 cc pressure reactor containing 5.0g of a solid acid catalyst. Each mix was heated to 120° C. and held at temperature for 4 hours. The reactor was then cooled, the product recovered, filtered and the liquid analyzed.

Results are summarized in Table II.

TABLE II

Propylene Glycol Monoalkyl Ethers Preparation

| Example | Acid Catalyst | Temp. (°C.) | $C_4^-$ | PG | t-BuOH | PGDiBu Ether | PGBuEther 1-OH | PGBuEther 2-OH | Total product wt (g) |
|---|---|---|---|---|---|---|---|---|---|
| 8 | XN-1010[a] | 120 | 3.9 | 16.3 | 23.1 | 0.8 | 1.1 | 8.9 | 103 |
| 9 | IR-118[b] | 120 | 3.5 | 17.8 | 25.4 | 0.7 | 1.1 | 8.6 | 102 |
| 10 | Nafion[c] | 120 | 4.8 | 13.5 | 24.0 | 0.7 | 0.9 | 7.0 | 105 |
| 11 | ZrCl$_4$/Clay-24[d] | 120 | 3.9 | 10.2 | 22.6 | 0.5 | 0.7 | 5.4 | 102 |
| 12 | W-P/Clay-24[e] | 120 | 3.8 | 15.6 | 21.5 | 0.7 | 1.0 | 8.3 | 103 |

[a] AMBERLYST ® XN-1010 macroreticular resin
[b] AMBERLITE ® IR-118 gel type resin
[c] NAFION ® NR50 beads, 20-35 mesh
[d] A zirconium (IV) chloride treated Engelhard Clay-24, granules
[e] A 12-tungsstophosphoric acid treated Engelhard Clay-24, granules

| 1-(t-butoxy)-2-propanol | 9.3% |
|---|---|
| 2-(t-butoxy)-1-propanol | 1.1% |
| Propylene glycol | 14.6% |
| t-Butanol | 22.1% |
| Isobutylene | 7.5% |

Estimated selectivity to propylene glycol mono-t-butyl ethers=25%.

EXAMPLES 6 AND 7

Synthesis Propylene Glycol Mono-t-Butyl Ethers

Following the procedures of Example 5, propylene oxide (58.0 g, 1.0 mole), distilled water (20.0g) and isobutylene (28.0 g, 0.5 mole) were charged to a 300 cc pressure reactor containing 12-tungstophosphoric acid (5.0g) and the mixture heated to a prescribed temperature with mixing. After 4 hours at temperature, the reactor was cooled and the product recovered and the liquid analyzed.

EXAMPLE 13

To a 300 cc pressure reactor fitted with heating, mixing and temperature control was charged a mixture of propylene oxide (58.0 g, 1.0 mole), distilled water (20.0g) and 12-molybdophosphoric acid (5.0g). The reactor was flushed with nitrogen and pressured with isobutylene (28.0 g, 0.5 mole), then heated to 100° C. with mixing. After 4 hours at temperature, the reactor was cooled and the product (113 g) recovered.

Analyses of the deep blue liquid product by GC showed the present of:

| Propylene Glycol Mono-t-Butyl Ethers: | |
|---|---|
| 1-(t-butoxy)-2-propanol | 5.6% |
| 2-(t-butoxy)-1-propanol | 0.2% |
| Propylene glycol di-t-butyl ether | 0.7% |
| Propylene glycol | 2.4% |
| t-Butanol | 20.1% |
| Isobutylene | 3.5% |

| Analyses of the off-gas samples showed the pressure of: | |
|---|---|
| Isobutylene | 24.8% |
| Propylene Oxide | 1.8% |

EXAMPLE 14

Synthesis Of Ethylene Glycol Mono-t-Butyl Ether

To a 300 cc pressure reactor fitted with heating, mixing and temperature control was charged a mixture of acidic montmorillonite clay (Engelhard, Clay-24 granules, 5.0g) and distilled water (20.0g). The reactor was flushed with nitrogen and pressured with ethylene oxide (44.0 g, 1.0 mole) plus isobutylene (28.0 g, 0.5 mole), then heated to 180° C. with mixing. After 4 hours at temperature, the reactor was cooled and the product (75.0g) recovered.

After removal of the clay granules, the pale yellow liquid product was analyzed by gc and gc-ir. Analysis showed the presence of:

| Ethylene glycol mono-t-butyl ether | 13.7% |
|---|---|
| Ethylene glycol di-t-butyl ether | 0.9% |
| Ethylene glycol | 22.5% |
| Isobutylene | <1% |
| t-Butanol | 30.4% |

Also present were significant quantities of diethylene glycol and triethylene glycol as well as the corresponding diethylene glycol mono-t-butyl ethers and triethylene glycol mono-t-butyl ethers.

EXAMPLE 15

Synthesis Of Ethylene Glycol Mono-t-butyl Ether

To a 300 cc pressure reactor fitted with heating, mixing and temperature control was charged a mixture of 12-tungstophosphoric acid (5.0 g) and distilled water (20.0 g). The reactor was flushed with nitrogen and pressured with ethylene oxide (44.0 g, 1.0 mole) plus isobutylene (28.0 g, 0.5 mole), then heated to 120° C. with mixing. After 4 hours at temperature, the reactor was cooled and the product (92.0g) recovered.

The pale yellow liquid product was analyzed by gc and gc-ir. Analysis showed the presence of:

| Ethylene glycol mono-t-butyl ether | 9.9% |
|---|---|
| Ethylene glycol di-t-butyl ether | 2.3% |
| Ethylene glycol | 9.7% |
| Isobutylene | 29.3% |
| t-Butanol | 25.3% |

Also present were significant quantities of diethylene glycol and triethylene glycol as well as the corresponding diethylene glycol mono-t-butyl ethers and triethylene glycol mono-t-butyl ethers.

EXAMPLE 16

Synthesis Of Propylene Glycol Monoisopropyl Ethers

To a 300 cc pressure reactor fitted with heating, mixing and temperature control was charged a mixture of propylene oxide (58.0 g, 1.0 mole), distilled water (20.0 g) and acidic montmorillonite clay (Engelhard Clay-24 granules, 5.0 g). The reactor was flushed with nitrogen and pressured with propylene (21.0 g, 0.5 mole), then heated to 150° C. with mixing. After 4 hours at temperature, the reactor was cooled and the product (87.4 g) recovered.

After removal of the clay granules by filtration, the pale yellow liquid product was analyzed by gc and gc-ir. Analysis showed the presence of propylene glycol monoisopropyl ethers, both 1-(isopropoxy)-2-propanol and 2-(isopropoxy)-1-propanol.

What is claimed is:

1. A process for the synthesis of propylene glycol mono-t-butyl ethers from isobutylene and propylene oxide which comprises:

contacting said isobutylene and propylene oxide in the presence of sufficient water to satisfy the stoichiometry of the reaction and a catalyst consisting essentially of 12-tungstophosphoric acid, and heating to 100° C. with mixing at a pressure of from 100 to 400 psig.

* * * * *